TODO

(56) References Cited

OTHER PUBLICATIONS

Supplementary European Search Report for European Patent App. No. 10826718.8 (Jul. 22, 2013).

International Preliminary Report on Patentability and Written Opinion (English translation) for PCT Patent App. No. PCT/JP2010/068964 (Jan. 18, 2011).

Office Action from Chinese Patent App. No. 201080049284.3 (May 31, 2013) and English translation thereof.

Office Action from Chinese Patent App. No. 2010800492843 (Aug. 13, 2014) with English language translation thereof.

Office Action from Chinese Patent App. No. 2010800492843 (Feb. 28, 2015) with English language translation thereof.

* cited by examiner

| OLIGO | SEQUENCE | °C | SEQ ID NO. |
|---|---|---|---|
| D1_1 | TGTTCTCTGACCAATGAATCTGC | 57.9 | 81 |
| D1_2 | TGGAACTGGGAACGCTTTAGATG | 59.8 | 15 |
| D1_3 | TTCGCTTCGTTGTAATTTCGGAC | 58.7 | 52 |
| D1_4 | AGGCATCCTAAGAAATCGCTACT | 58.4 | 66 |
| D1_5 | TAGCCCAGTGATTTATGACATGC | 57.8 | 83 |
| D1_6 | CGCTCTGGTTACTATTGGACGTT | 59.5 | 23 |
| D1_7 | TAGCCAACTCTAAATAACGGACG | 57.1 | 99 |
| D1_8 | TTCGGTTGTCGATATGAGGATCT | 58.1 | 72 |
| D1_9 | GGGGGGTACTTCATACAAGATGC | 59.7 | 17 |
| D1_10 | GAGTAGCAGGCAAATACCCTAGA | 58.4 | 67 |
| D1_11 | GCCTATTAAGGTCTACGTCATCG | 57.2 | 96 |
| D1_12 | AGTCATACAGTGAGGACCAAATG | 57.1 | 98 |
| D1_13 | CATTCGACATAAGCTGTTGATGC | 57.3 | 93 |
| D1_14 | TGCTCACTTACATTACGTCCATG | 57.6 | 85 |
| D1_15 | TACACCTATCAACTCGTAGAGCA | 57.4 | 90 |
| D1_16 | AGGTCCGGTAGTAATTTAGGTGC | 58.8 | 49 |
| D1_17 | TGCACTCTGATATATACAGGCCA | 57.9 | 78 |
| D1_18 | GCAGCCCTTATAGATAACGGGAC | 58.5 | 24 |
| D1_19 | GAAGCCATGATACTGTTCAGGGT | 59.4 | 32 |
| D1_20 | TATTCTACCAACGACATCACTGC | 57.3 | 92 |
| D1_21 | CCATCAGTTATTCGGAGGGACTC | 59.1 | 44 |
| D1_22 | CCATATCCGATTATTAGCGACGG | 57.6 | 84 |
| D1_23 | CATCTCCAAGAATTGACCCACCA | 59.6 | 19 |
| D1_24 | CCGTCGTGTTATTAAAGACCCCT | 59.3 | 40 |
| D1_25 | GAAGGATCGCTTTTATCTGGCAT | 58.0 | 74 |
| D1_26 | CATTTGTCAGGTACAGTCCACTT | 57.5 | 86 |
| D1_27 | GCCCACACTCTTACTTATCGACT | 58.7 | 51 |
| D1_28 | CGCTGTTACTGTAAGCGTACTAG | 57.5 | 88 |
| D1_29 | CGCGATTCCTATTGATTGATCCC | 58.3 | 68 |
| D1_30 | CCGTCTGGGTTAAAGATTGCTAG | 57.9 | 79 |
| D1_31 | AGTCAGTCCAAATCTCAGGATGG | 58.9 | 48 |
| D1_32 | CGCCTAAATGAAACTCACTCTGC | 58.8 | 50 |
| D1_33 | GGGGTCAAACCAACAATTGATCT | 58.4 | 64 |
| D1_34 | GCCATTGATAGAATTACGAGGC | 58.3 | 69 |
| D1_35 | ATGCCGTTGTCAAGAGTTATGGT | 59.5 | 20 |
| D1_36 | TGCCGGCTATCGTAAGTATATGC | 59.2 | 42 |
| D1_37 | GCACCTCATACCTTCATAGAGCA | 58.9 | 47 |
| D1_38 | CGCGACATTTAGTCCAGGAGATG | 60.0 | 11 |
| D1_39 | CTAGTCCATTGTAACGAAGGCA | 59.3 | 39 |
| D1_40 | AGACAATTAGAATCAGTGCCCCT | 58.6 | 53 |
| D1_41 | GCATTGAGGTATTGTTGCTCCA | 60.4 | 5 |
| D1_42 | CGAGAGTCTGTAATAGCCGATGC | 59.5 | 21 |
| D1_43 | TGCCGTGATACTTAACTACGCTA | 58.2 | 71 |
| D1_44 | GAGTCCGCAAAAATATAGGAGGC | 58.3 | 70 |
| D1_45 | GCCTCACATAACTGGAGAAACCT | 59.3 | 34 |
| D1_46 | CGCCAATGACAATAAGTTGAGGC | 59.4 | 30 |
| D1_47 | GCCGATATAACATTAACCGAGGC | 58.5 | 63 |
| D1_48 | CACGCTTAGTTCCTACCTTAGGC | 59.5 | 22 |
| D1_49 | CGCGTGAATTACTTAATCACCA | 58.0 | 73 |
| D1_50 | GGGATAGGTATTATGCTCCAGCC | 59.1 | 43 |
| D1_51 | CGCCATTATACAACGGTTCATGC | 59.4 | 27 |
| D1_52 | GCCTATATGAACCAAGCCACTGC | 60.7 | 1 |
| D1_53 | CGCCGTCAGTACTTGTATAGATG | 57.4 | 91 |
| D1_54 | GTCGGTATCGAAAAGGTACTGCA | 59.4 | 29 |
| D1_55 | AGGCAGTTCAACCTATATCTGCG | 59.4 | 33 |
| D1_56 | GGTCGTAACATTGAGAGGAGACG | 59.4 | 31 |
| D1_57 | GGCGATTTATTGCTAACTGGCTA | 58.0 | 75 |
| D1_58 | GCACTACCGCTAACTATACGCTA | 58.5 | 60 |
| D1_59 | GGCTCGTAGTACTCCTTACATGC | 59.3 | 38 |
| D1_60 | GGCTCTACAAACTTGTGTCCATG | 58.6 | 56 |
| D1_61 | GGTGGAGTGAATCTCACTAGACT | 58.0 | 76 |
| D1_62 | CTAGCACAATTAATCAATCCGCC | 56.9 | 100 |
| D1_63 | GCAGCTGAATTGCTATGATCACC | 59.0 | 46 |
| D1_64 | GCCTATAGTGTCGATTGTCCTCG | 59.3 | 37 |
| D1_65 | CGATCACGGATTAATGTCACCCC | 60.1 | 9 |
| D1_66 | AAGAGATTTAACTTGAGCTCGCC | 57.9 | 80 |
| D1_67 | TTTGTTGTTCGATATCAGGCGTG | 58.5 | 59 |
| D1_68 | GCCCGGGAATAGATTATAACGCA | 59.5 | 23 |
| D1_69 | GCATTTTTAGTAATCCGAGCGCC | 59.4 | 26 |
| D1_70 | CATGGATAAGTTTTCAAGCTGCG | 57.5 | 87 |
| D1_71 | GAGACAGGTAAACCCTCAGACA | 60.7 | 2 |
| D1_72 | TAGCACCCGTTAAAACGGAAATG | 58.6 | 58 |
| D1_73 | TATGTTTAGTTGTTGAACCGGCG | 58.5 | 61 |
| D1_74 | CGATCAGCTCTATTTCCCTCCCA | 60.6 | 4 |
| D1_75 | AGTCAGTTAATCAGACGTGAGCA | 58.6 | 54 |
| D1_76 | TGGCAATACAATAACGTATCGCG | 58.4 | 65 |
| D1_77 | CGCAGTTTGCAAGAACGAACAAA | 60.1 | 10 |
| D1_78 | CGCGATAATTGATACCTACGGGC | 60.2 | 8 |
| D1_79 | GGGGTGTGAGAGCTTTTTAGACG | 60.2 | 7 |
| D1_80 | GGGATCCGTAACAAGTGTGTTAG | 57.8 | 82 |
| D1_81 | ACCACTATGATTGASGGAAACGCG | 60.0 | 12 |
| D1_82 | CGTCTTTAGTATCAACCCTCCGC | 59.8 | 16 |
| D1_83 | GCATACGAACTTCTATATCGGCG | 58.0 | 77 |
| D1_84 | CCGTGTGTATGAGTATGACAGCA | 59.2 | 41 |
| D1_85 | TGCTGTCTTCGTGTTTTACCTAG | 57.4 | 89 |
| D1_86 | CGATCATGTAAAGCTAACTCGCG | 58.6 | 57 |
| D1_87 | TGCCGTCATTTAAACGTAAGGGT | 59.7 | 18 |
| D1_88 | TGGCAATTACAGTTGTTAACGCA | 58.5 | 62 |
| D1_89 | GAGTCGAAGACCTCCTCCTACTC | 59.9 | 14 |
| D1_90 | ATGCCAATATGTACTCGTGACTC | 57.2 | 97 |
| D1_91 | GCATATAGTGACGGTAAGGCGAA | 59.3 | 35 |
| D1_92 | GCCTCACTTGTAATAAGCGGGAC | 60.3 | 6 |
| D1_93 | GTCCCAAAAGCTTCTTACGGACG | 60.6 | 3 |
| D1_94 | CTAGGTACAACACCAACTGTCTC | 57.2 | 95 |
| D1_95 | TGCCGGTTATACCCTTAAGGACG | 59.3 | 36 |
| D1_96 | GGCTGGTTAAATGTAAATCCGCG | 59.4 | 28 |
| D1_97 | CGCGGTACTATTAGAAAGGGCTA | 58.6 | 55 |
| D1_98 | AGTCGCTTAATTACTCCGGATGG | 59.1 | 45 |
| D1_99 | CGCTGTTGGTATTACCTTCCTCG | 60.0 | 13 |
| D1_100 | TGCAGTGTAAGCAACTATTGTCT | 57.3 | 94 |

FIG. 5

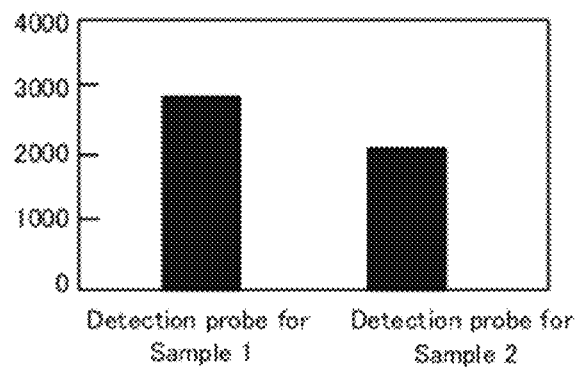
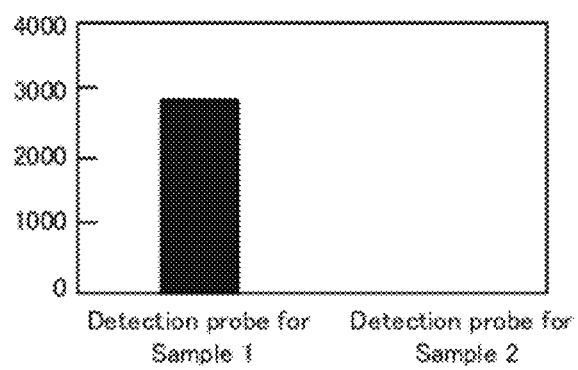
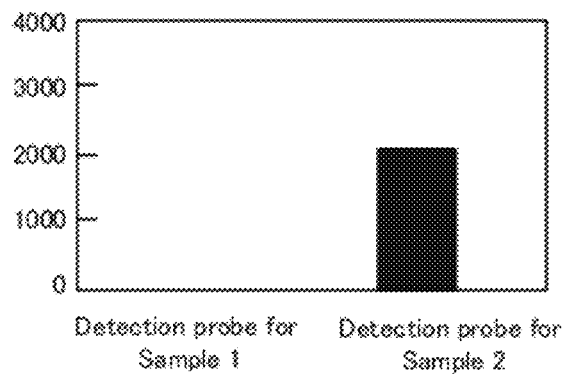
Fig.6

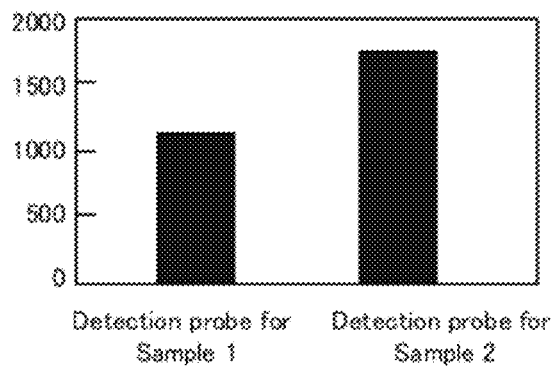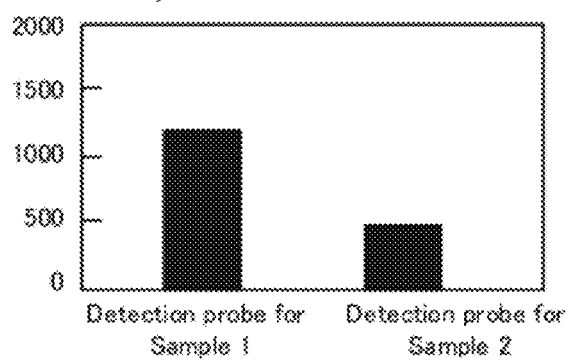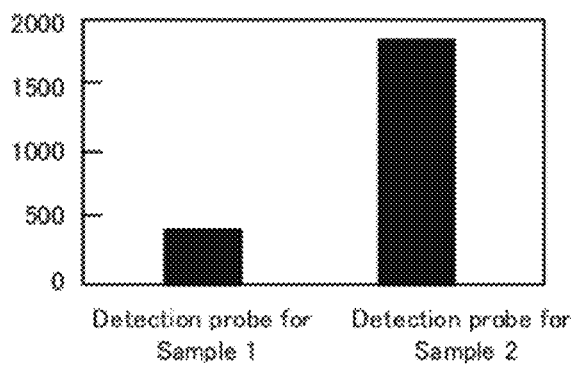
Fig.7

METHOD FOR DETECTION OF TARGET NUCLEIC ACID

This application is a national phase entry under 35 U.S.C. §371 of PCT Patent Application No. PCT/JP2010/068964, filed on Oct. 26, 2010, which claims priority under 35 U.S.C. §119 to Japanese Patent Application No. 2009-249122, filed Oct. 29, 2009, both of which are incorporated by reference. Also, the Sequence Listing filed electronically herewith is hereby incorporated by reference (File name: 1027-0022_Seq_List_2012-03-19; File size: 18 KB; Date recorded: Mar. 19, 2012).

TECHNICAL FIELD

The present application claims priority to Japanese Patent Application No. 2009-249122 filed on Oct. 29, 2009, which is incorporated herein by reference in its entirety. The present invention relates to a technology for detecting target nucleic acids.

BACKGROUND ART

It has been conventionally proposed to exhaustively detect or quantitate nucleic acid sequences in order to carry out genetic analyses of individual organisms and to test an infection of biological samples with viruses or bacteria. For example, microarrays (hereinafter merely referred to as "arrays") are used for detecting an expression level of nucleic acid sequences to be detected (target nucleic acids) in samples (e.g., see Non-patent documents 1 to 4) Arrays are carriers on which multiple nucleic acid fragments (detection probes) having known base sequences are independently fixed. As shown in FIG. 8, in conventional array methods, a forward primer (F primer) and a reverse primer (R primer) designed so as to flank the target sequence are used to amplify a DNA fragment (target nucleic acid) containing the target sequence. The amplified nucleic acid is then separated to a single strand. The target nucleic acid then binds on the carrier by hybridization of the target sequence with a portion complementary to a partial sequence characteristic to the target nucleic acid (target sequence). The hybridized target nucleic acid is detected by any suitable method to determine a presence or absence of the nucleic acid in the sample. Arrays specific for detection of single nucleotide polymorphisms (SNPs) have been developed (e.g., see Patent documents 1 and 2). By this method, a type of SNPs of the target nucleic acid in the sample can be detected by using DNA computer technology.

CITATION LIST

Patent Literature

Patent document 1: Japanese Patent Application Laid-open No. 2006-211982
Patent document 2: Japanese Patent Application Laid-open No. 2006-101844

Non Patent Literature

Non-patent document 1: Baio Jikken de Shippai Shinai!Kenshutsu to Teiryo no Kotsu (Successful Biotechnological Experiments: Tips for Detection and Quantification), Supplementary volume of Jikken Igaku (Medical Experiments), Yodosha, Chapter 3, 10. Maikuroarei no Kotsu (Tips for Microarrays)

Non-patent document 2: Bioview, No. 45, pp 14-18, 2004, Takara-Bio

Non-patent document 3: Biotechnology series: DNA chip application technology, CMC Publishing, Chapter 5, Practice an application of DNA microarrays Non-patent document 4: Ministry of Health, Labour and Welfare Grant-in-Aid for Scientific Research, Research project on securement of food safety and reliability (Annual Report of Ministry of Health, Labour and Welfare, 2006)

SUMMARY

In the methods disclosed in Non-patent documents 1 to 4, the detection probe fixed on the array is hybridized with the target sequence, which hybridization requires a prolonged period of time. In addition, the detection probe may bind non-specifically to other nucleic acid sequences having similarity (homology) with the target sequence. Namely, upon detection of multiple target sequences in the sample, the presence or absence thereof may not be accurately detected.

Regarding the non-specific binding problems, Non-patent document 2 discloses that homology of the detection probe can be minimized by reducing a length thereof. However, the reduction in the length of the detection probe may decrease an intensity of signal of a label upon detection. Non-patent document 4 discloses that non-specific binding may be decreased by increasing hybridization temperature. However, when the problem is not solved by these methods, the sequence of the detection probe needs to be re-designed and the array needs to be re-prepared. Thus, users of arrays need to consider an influence of homology, making process steps for obtaining an appropriate detection system for the target nucleic acid significantly intricate.

On the other hand, the methods disclosed in Patent documents 1 and 2 are specific for detection of SNPs, which allow accurate detection of SNPs. However, seven different probes are required for the detection of one SNP and procedures are further intricate. In addition, to design probes is troublesome because it is required for the user to ligate amplification byproducts of the target nucleic acid before hybridization of the target nucleic acid to the array.

As described above, a lot of effort is required in conventional methods for constituting the detection system of intended target nucleic acids. It has been also difficult to accurately detect the target nucleic acid in a short time. Accordingly, an object of the disclosure of the present specification is to provide a method for detection of the target nucleic acid allowing effective construction of the detection system of the target nucleic acid.

The present inventors have studied in order to effectively construct the detection system on various methods which allow effective hybridization of the detection probe fixed on the carrier with the target nucleic acid while maintaining selectivity. As a result, they have reached to a conclusion that it is difficult to effectively construct the detection system based on a hybridization reaction due to sequence specificity of the target nucleic acid on a solid carrier. They have also found that consideration on hybridization conditions may be omitted and non-specific binding may be excluded and high selectivity can be achieved by using multiple sets of detection probes and tag sequences which have been designed so as to be able to specifically hybridize and attaching the tag sequences to the target nucleic acid. In addition, without requiring ligation of such a chimeric target nucleic acid using a probe specific to the target sequence, non-specific binding between the labeled target nucleic acid and the detection probe can be reduced by amplifying the labeled target nucleic acid using primers specifically hybridizable to a partial sequence having low homology, i.e. a sequence characteristic to the target nucleic acid. The following method is provided based on these findings.

The disclosure of the present specification relates to a method for detection of the target nucleic acid in the sample. The present method for detection comprises steps of preparing a solid phase comprising detection probes respectively having certain different base sequences, carrying out PCR on the sample to obtain chimeric DNAs each having a label and a tag sequence complementary to each of the detection probes having been correlated to the target nucleic acid, bringing the chimeric DNAs into contact with the detection probes such that the chimeric DNAs and the detection probes can hybridize through the tag sequences, obtaining signal intensity information based on the label on the solid phase, and detecting the target nucleic acid based on the signal intensity information.

The step of PCR comprises preparing a first primer having an identification sequence complementary to the target sequence in the target nucleic acid and a tag addition sequence complementary to the tag sequence, and a second primer having a partial sequence identical to a partial sequence adjacent to the target sequence and the label, and carrying out PCR on the sample using the first primer and the second primer to synthesize the chimeric DNA having the target sequence, the tag sequence and the label.

In the step of PCR, two or more first primers and one second primer common to the two or more target nucleic acids may be used for two or more target nucleic acids.

The step of PCR may be the step of amplifying the chimeric DNAs by asymmetric PCR.

The target nucleic acid can be detected by using the array comprising the detection probe hybridizable to the tag sequence having been correlated to the target nucleic acid.

BRIEF DESCRIPTION OF DRAWINGS

FIG. 5 is a table showing base sequences of detection probes;

FIG. 6 is a view showing detection results obtained in examples of the present invention;

FIG. 7 is a view showing detection results obtained in examples of the conventional method.

DESCRIPTION OF EMBODIMENTS

The present invention relates to the array for detection of the target sequence in the target nucleic acid which is to be detected. According to the method for detection of the target nucleic acid of the present invention, a procedure can be avoided for constructing the detection system by designing the detection probes having different unique base sequences respectively for all target nucleic acids and fixing them on the solid phase carrier. By carrying out PCR on the sample so as to obtain the chimeric DNA having a detection sequence complementary to the detection probe having been correlated to the target nucleic acid and the label, the target nucleic acid can be identified and the chimeric DNA which has the detection sequence having been correlated to the detection probe, is specific to the target nucleic acid and is labeled can be obtained by PCR for preparation of DNA for hybridization. By hybridizing the chimeric DNA and the detection probe via the detection sequence, the chimeric DNA hybridizes to the detection probe based on the detection probe and the detection sequence which have been correlated to each other, effectively suppressing or avoiding non-specific binding upon hybridization.

According to the disclosure of the present specification, the first primer having the identification sequence complementary to the target sequence in the target nucleic acid and the tag addition sequence and the second primer having the partial sequence adjacent to the target sequence and the label are used when PCR is carried out, thereby suppressing or avoiding complicated design of probes or primers. The set of primers allows easy preparation of the chimeric DNAs for hybridization with the detection probes which directly identify the target sequences and are specific to the target nucleic acids.

This method ensures detection of each of multiple target nucleic acids and can be used for detection of single nucleotide polymorphisms (SNPs) or modified sites in genetically modified nucleic acids or for detection of expression genes such as RNAs. Namely, SNPs, modified sites, expression genes, polymorphisms or mutations in the target nucleic acids can be detected by obtaining chimeric DNAs based on the same concept as the detection of the mutation to be detected.

Figure 4:
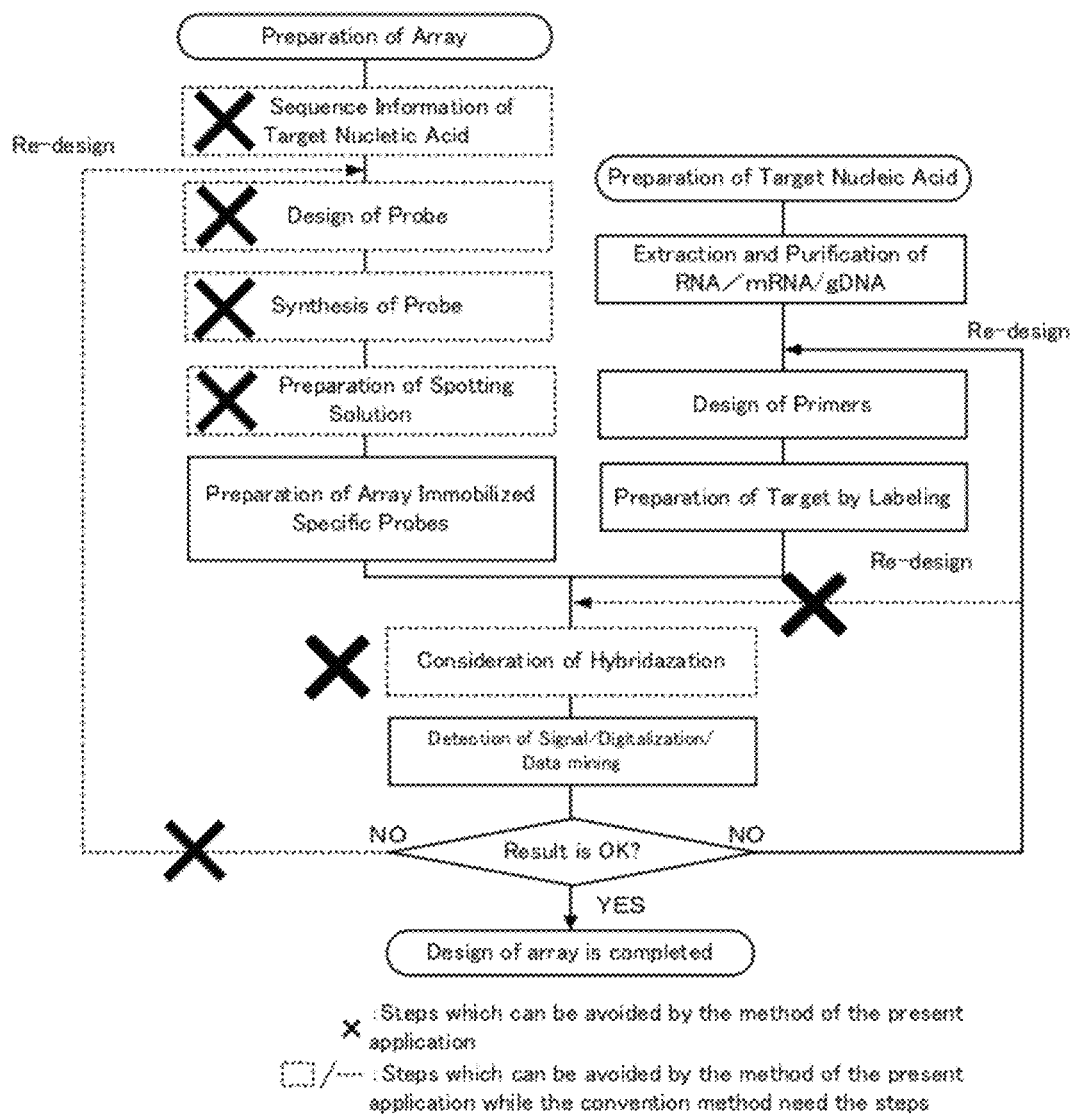
FIG. 4 is a flow chart for preparation of the array and the target.
Figure 8:
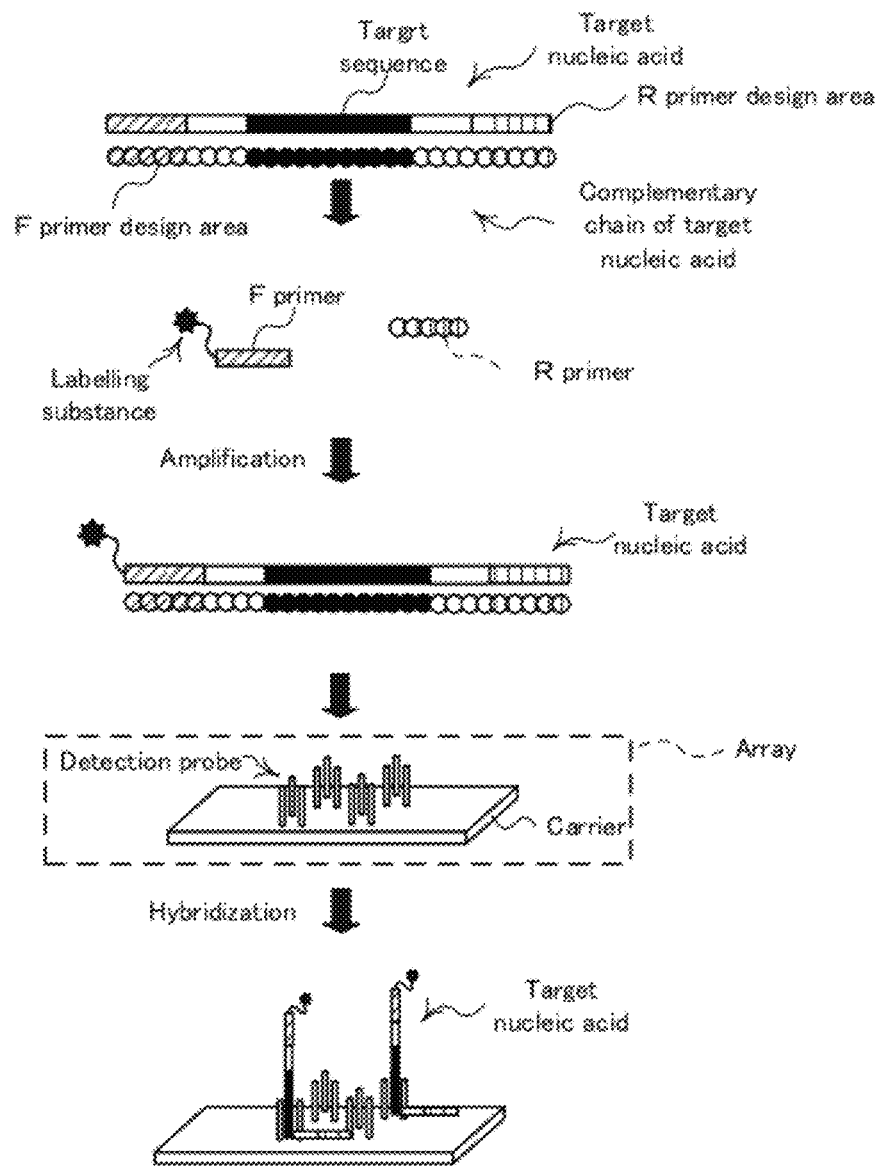
FIG. 8 is a view showing an exemplary conventional detection method of target nucleic acids.

FIG. 4 shows an outline of the procedures of the preparation of the array and the target for detection of the target nucleic acid. FIG. 4 also shows the flow chart for the method disclosed in the present specification as well as the conventional detection method. The steps shown with the solid line are the steps common for the method disclosed in the present specification and the conventional method, and the steps shown with the dashed line are the ones necessary only for the conventional method. In the conventional method, multiple steps are carried out for preparation of arrays for respective target nucleic acids. Information on the sequence of the target nucleic acid to be detected is first obtained and the detection probe is designed according to the sequence information. The detection probe is then synthesized according to the design and prepared in a spot solution for the array in order to fix the probe on the array. Meanwhile the target nucleic acid to be detected (a target such as RNA or DNA) is extracted and purified from the sample. Primers for amplifying the target nucleic acid are designed and synthesized with a labeling. The target nucleic acid is then amplified with the synthesized primers. The amplified target nucleic acid is then hybridized with the detection probe on the array prepared (hybridization). The occurrence of hybridization is examined according to detection of signal of the label on the array and the obtained signal of the label is converted to the numeral value. When the obtained results are not the ones expected such as abnormal or absence of fluorescence signal etc., the array has to be designed again or the sample has to be prepared again, as shown with the solid and dashed lines in FIG. 4.

The conventional methods disclosed in Non-patent documents 1 to 4 require many reviews on hybridization conditions, primers, and even sequences of the detection probes on the array. It takes a prolonged period of time to re-design and synthesize oligo DNAs for the detection probes and query probe sequences. According to the present method, the detection probes and query probes may be merely selected from 100 different sequences (see Sequence Listing). The methods disclosed in Patent documents 5 and 6 require seven different primers and probes for detection of one target sequence. However, the present invention requires only two kinds of primers for detection of one target sequence.

On the other hand, the method disclosed in the present specification merely requires preparation of the array comprising multiple detection probes respectively having the unique detection sequence preliminarily determined regardless of the target nucleic acid. As the array can be applied regardless of the target nucleic acid, design, synthesis and fixation of probes for respective target nucleic acids and review of hybridization conditions may all be avoided, unlike the conventional a method. The detection system may be constructed according to the method disclosed in the present specification by mainly considering only the design of the primers upon preparation of the target.

According to the method disclosed in the present specification, the detection probes can be prepared for which hybridization conditions are optimized, thus the target nucleic acid can be accurately detected in a short time.

As used herein, the "nucleic acid" includes all DNAs and RNAs including cDNA, genomic DNA, synthetic DNA, mRNA, total RNA, hnRNA and synthetic RNA as well as artificial synthetic nucleic acids such as peptide nucleic acid, morpholino-nucleic acid, methylphosphonate-nucleic acid and S-oligo nucleic acid. The nucleic acid may be single-stranded or double-stranded. As used herein, the "target nucleic acid" is any nucleic acid having any sequence. Typically, the target nucleic acid includes nucleic aids which may have base sequences genetically indicative for constitution or disease incidence, disease diagnosis, disease prognosis, drug or treatment selection of specific diseases such as genetic diseases or cancer in human or non-human animals. The genetically indicative base sequences include polymorphisms such as SNPs and inherent or acquired mutations. The target nucleic acid also includes nucleic acids derived from microorganisms such as pathogens and viruses.

The target nucleic acid may be the sample described below or a nucleic acid fraction thereof and is preferably an amplified product in which all of the multiple target nucleic acids have been amplified by preferably amplification reaction with PCR, more preferably multiplex PCR.

As used herein, the "sample" refers to the sample which may contain the target nucleic acid. The sample may be any sample containing a nucleic acid including cells, tissues, blood, urine, saliva and the like. A person skilled in the art may appropriately obtain a fraction containing the nucleic acid from such various samples according to the conventional art.

As used herein, the "target sequence" refers to a sequence formed by one or more bases characteristic to the target nucleic acid to be detected. The target sequence may be a partial sequence having low homology among the target nucleic acids or a sequence having low complementarity or homology to other nucleic acids which may be contained in the sample. The target sequence may be a sequence characteristic to the target nucleic acid. The target sequence may have a sequence artificially modified.

Representative and non-limiting specific examples of the disclosure of the specification are described herein after with referring to the drawings. The detailed description merely intends to illustrate the details to a person skilled in the art for carrying out the preferred examples of the disclosure of the present specification, while it does not intend to limit the scope of the disclosure of the present specification. Additional features and disclosures hereinafter may be used separately or in conjunction with other features or inventions in order to provide a further improved method for detection of the target nucleic acid and the like.

Combinations of the features and steps disclosed hereinafter in the detailed description are not requisite for carrying out the disclosure of the present specification in its broadest meaning, but are particularly described merely for illustrating representative specific examples of the disclosure of the present specification. Various features of the above- and below-described representative specific examples as well as various features of those described in independent and dependent claims are not the ones which have to be combined as the specific examples or in the same order as described herein in order to provide additional and useful modes of the disclosure of the present specification.

All features described in the present specification and/or claims intend to be disclosed, individually and independently each other, as limitations for specific items described in the disclosure and claims at the time of filing the present application, separately from a structure of the features described in examples and/or claims. Descriptions on all numerical ranges and groups or sets intend to disclose intermediate aspects thereof as limitations for specific items described in the disclosure and claim at the time of filing the present application.

Figure 1:
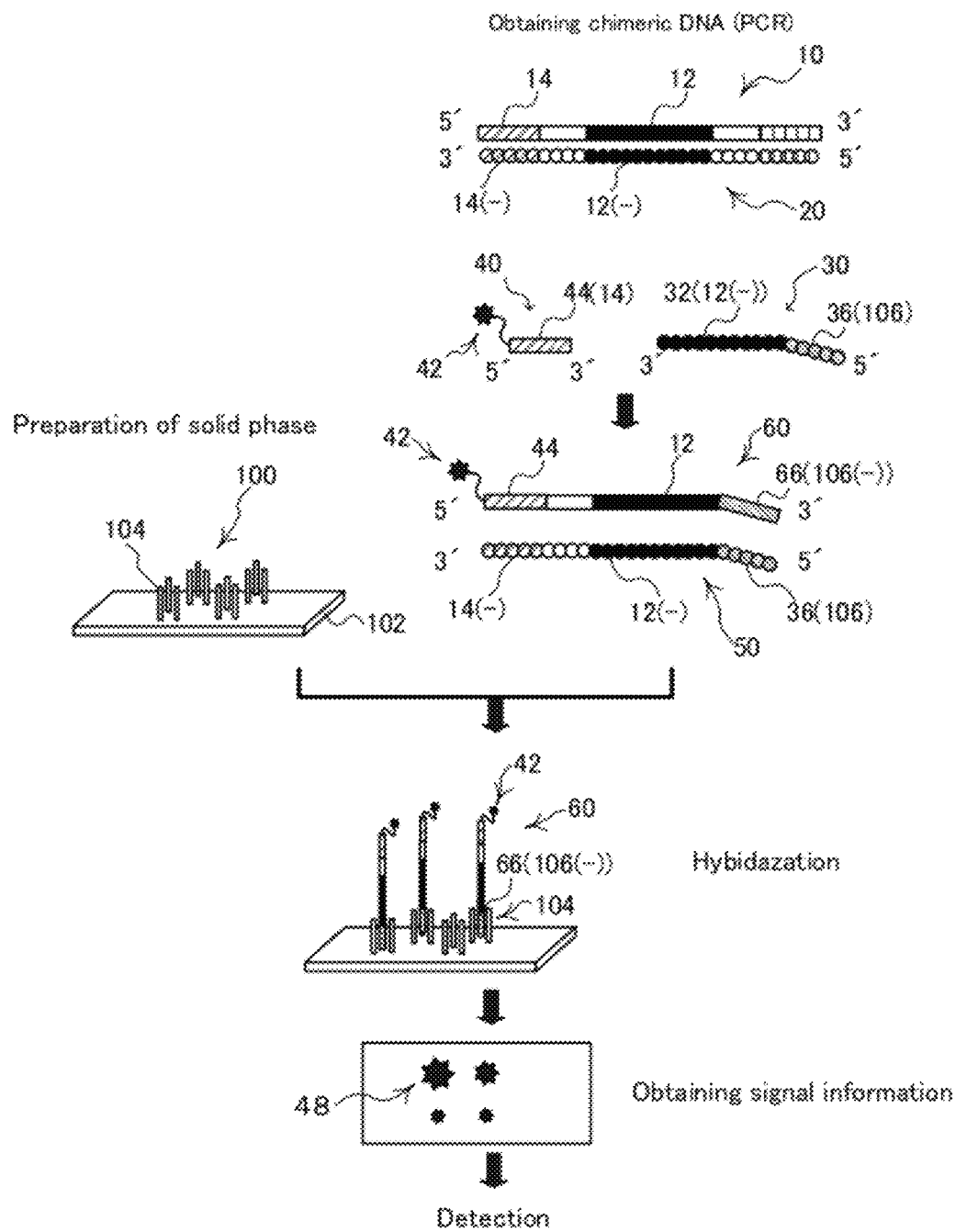
FIG. 1 is a schematic view of an example of the method for detection of the present invention.
Figure 2:
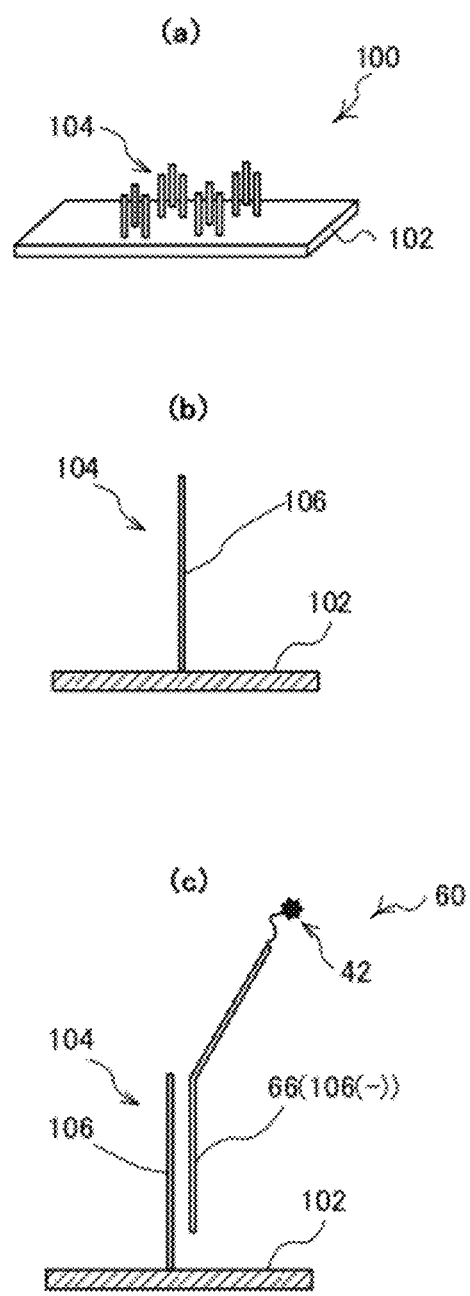
FIG. 2 is a view depicting relationship between the solid phase carrier, and the detection probes and the chimeric DNA on the solid phase carrier according to the present invention.
Figure 3:
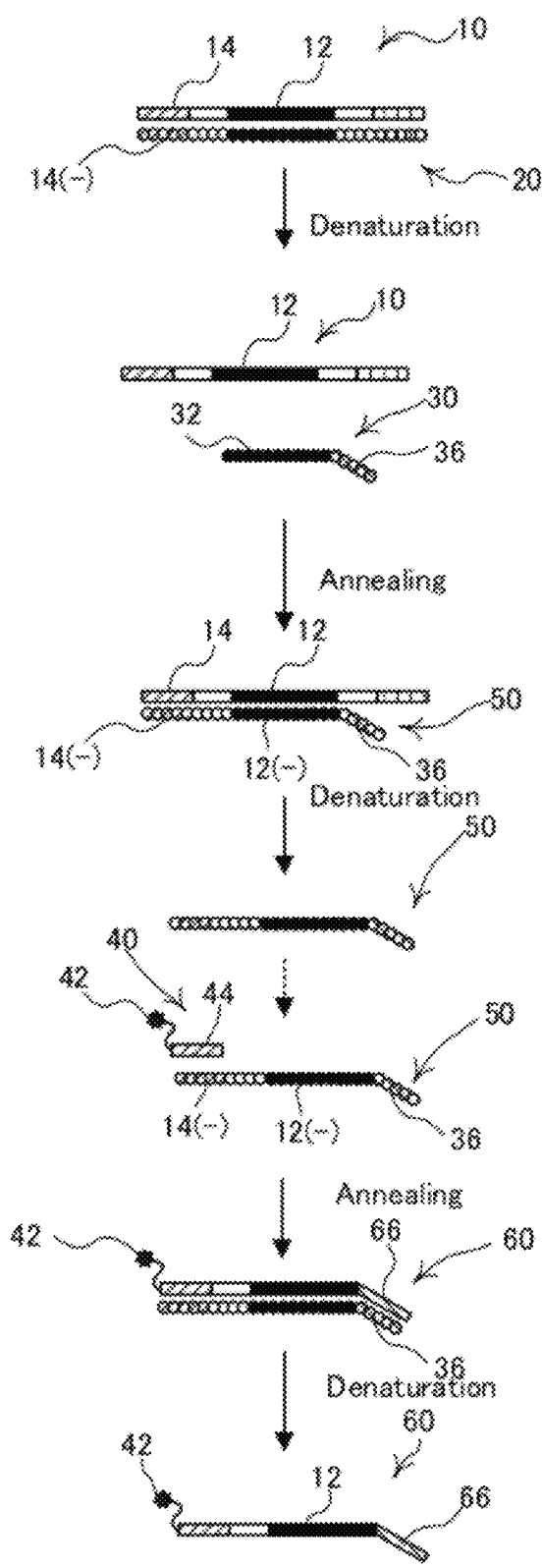
FIG. 3 is a view showing the step of amplification of the labeled target nucleic acid according to the preset invention.

FIG. 1 is a schematic view showing a principle of the method for detection of the present invention. FIG. 2 shows an example of the solid phase 100 used for the present invention and FIG. 3 shows details for the step of amplification in FIG. 1. FIGS. 1 and 3 show an example for the method for detection and the primer for detecting one target nucleic acid contained in the sample. In the descriptions hereinafter, a base sequence designated with a number and (-) means a complementary base sequence of a base sequence designated with the same number.

[Method for Detection of the Target Sequence in the Target Nucleic Acid]

The method for detection disclosed in the present specification comprises steps of preparing the solid phase comprising multiple detection probes respectively having different unique base sequences, carrying out PCR on the sample so as to obtain chimeric DNAs respectively having tag sequence complementary to the detection sequence of the detection probe having been correlated to the target nucleic acid and the label, hybridizing the chimeric DNAs and the detection probes through the detection sequence and the tag sequence, obtaining signal intensity information based on the label on the carrier, and detecting the target nucleic acid based on the signal intensity information. The method for detection according to the disclosure of the of the present specification is applied to one or more target nucleic acids and more specifically, aims to detect the target sequence(s) characteristic in the target nucleic acid(s). A series of the steps for detection of one target nucleic acid is mainly illustrated hereinafter. However, the steps described below may also be applied for simultaneous detection of several or many target nucleic acids.

(Step of Preparation of Solid Phase Carrier)

The method for detection disclosed in the present specification (hereinafter merely referred to as the present method for detection) may comprise the step of preparing the solid phase 100 as shown in FIG. 1. The solid phase 100 may be preliminary prepared prior to carrying out the method for detection, may be commercially obtained or may be prepared every time when carrying out the method for detection.

As shown in FIG. 1, the solid phase 100 may comprise multiple detection probes 104 respectively comprising the detection sequences 106 which are different unique base sequences on the carrier 102. Preparation of such a solid phase 100 may avoid design and synthesis of probes, preparation of arrays and consideration on hybridization conditions.

FIG. 2 shows an example of the solid phase 100. The detection probes 104 contain the detection sequences 106 which are respectively unique base sequences for probing. Such detection sequences 106 may be established irrespectively of the sequence characteristic to the target nucleic acid 10, i.e. the target sequence 12. The detection sequences 106 in the detection probes 104 are irrespective of the target sequence 12 and may be established so as to suppress or avoid non-specific binding between multiple detection probes 104 and obtain suitable hybridization conditions such as temperature and time. In addition, same detection probes 104 may be used all the time irrespective of the variation of the target nucleic acid 10.

The detection sequence 106 in the detection probe 104 may be base sequences of SEQ ID NO: 1 to SEQ ID NO: 100 or their complementary base sequences. These base sequences have the same base length and have a melting temperature (Tm) of 40° C. or higher and 80° C. or lower, more preferably 50° C. or higher and 70° C. or lower, thereby giving homogeneous hybridization results under the same hybridization conditions.

The detection sequence 106 in the detection probe 104 may be appropriately selected from such candidate base sequences. Two or more detection probes 104 to be used preferably have melting temperatures as close as possible to each other. When multiple target nucleic acids 10 are exhaustively and simultaneously detected, multiple detection probes 104 for respective multiple target nucleic acids 10 are preferably combined so as to have melting temperatures closest to each other. For example, when detection probes 104 are arranged in order of their melting temperatures, two or more detection probes 104 for respective two or more target nucleic acids 10 to be distinguished may be selected from two base sequences adjacent in the arrangement by melting temperatures. The detection sequence 106 in the detection probe 104 for another target nucleic acid 10 may be selected from base sequences immediately consecutive to or apart from the base sequence which has already been selected. It is also preferable to use the base sequences which have consecutive melting temperatures in the arrangement by the melting temperatures for all detection probes for multiple target nucleic acids 10 to be detected simultaneously.

The melting temperature may be the one calculated according to a GC % method, a Wallace method, a method according to Current Protocols in Molecular Biology (described in Biotechnology Experiments Illustrated 3, *Honto ni fueru* PCR (Truly amplifiable PCR), Shujunsha, p. 25); however, it is preferably calculated by a Nearest-Neighbor method to which impacts of a range of the melting temperature an a concentration of the base sequence in the present invention may be included. The melting temperature by the Nearest-Neighbor method can be easily obtained by using, for example, software equipped with Visual OMP (Tomy Digital Biology Co., Ltd.) or software provided by Nihon Gene Research Laboratories Inc. (http://www.ngrl.co.jp) (Oligo-Calculator, http://www.ngrl.co.jp/tool/ngr_tool.html). SEQ ID NO: 1 to SEQ ID NO: 100 are arranged in descending order of the melting temperatures calculated with Visual OMP (0.1 M probe concentration, 50 mM $Na^+$ ion and 1.5 mM $Mg_+$ ion).

The detection sequence 106 in the detection probe 104 is called as a orthonormalization sequence and is designed based on the calculations on a consecutive identical length, melting temperature prediction by the Nearest-Neighbor method, a Hamming distance, secondary structure prediction on DNA sequences having certain base lengths obtained from random numbers. The orthonormalization sequences are base sequences of nucleic acids which have homogeneous melting temperatures and thus are designed so as to have the melting temperatures in a constant range, which do not inhibit hybridization with the complementary sequences because nucleic acids are structured intramolecularly, and which do not stably hybridize with base sequences other than complementary base sequences. Sequences contained in one orthonormalization sequence group hardly react or do not react to sequences other than a desired combination or within their sequences. When orthonormalization sequences are amplified by PCR, the amount of the nucleic acids quantitatively amplified correspond to an initial amount of the nucleic acids having the orthonormalization sequences without influenced by a problem such as cross-hybridization as mentioned above. Such orthonormalization sequences are reviewed in H. Yoshida and A. Suyama, "Solution to 3-SAT by breadth first search", DIMACS Vol. 54, 9-20 (2000) and Japanese Patent Application No. 2003-108126. The orthonormalization on sequences can be designed by using the methods described in these documents.

The detection probes 104 are fixed on the carrier 102. The carrier 102 may be the solid phase carrier. The carrier 102 may be, for example, plastics, glass or any other material without limitation. A shape of the carrier 102 may be a plate as shown in FIG. 1 or may be a bead without limitation. The solid phase 100 is preferably the array (particularly microarray) in which the support 102 is a solid phase plate and multiple detection probes 104 are fixed with a regular sequence. The array can be fixed with many detection probes 104 and is suitable for detecting various target nucleic acids 10 simultaneously and exhaustively. The solid phase 100 may comprise multiple defined array regions on the carrier 102. On the multiple array regions, the same sets of detection probes 104 or different sets of detection probes 104 may be fixed. When different combinations of the sets of detection probes 104 are fixed on multiple array regions, individual array regions may be assigned for detection of target nucleic acids 10 in different genes.

The preferred solid phase 100 may comprise two or more detection probes 104 arranged in order of their melting temperatures. For example, by using such a solid phase 100 in which two or more detection probes 104 for two or more target nucleic acids 10 corresponding to two or more target sequences 12 which may exist at certain sites in certain genes are arranged in such order, variation in hybridization due to the difference in melting temperatures of detection sequences 106 in detection probes 104 or to position to where detection probes 104 are fixed is suppressed, thereby allowing accurate detection of target nucleic acids 10 in the sample.

The detection probes 104 may be fixed by any mode without limitation, which may be covalent or non-covalent. The detection probes 104 may be fixed on the surface of the carrier 102 by any various well-known methods in the art. The surface of the carrier 102 may comprise appropriate linker sequences. The linker sequences preferably have the same base length and same sequence for the respective detection probes 104.

(Step of Obtaining Chimeric DNA: Step of PCR)

As shown in FIG. 1, the step of PCR may comprise carrying out PCR on the sample so as to obtain the chimeric DNA 60 having the label 42 and the tag sequence 66 which is able to hybridize with the detection sequence 106 in the specific detection probe 104 having been correlated to the target nucleic acid 10. By obtaining such a chimeric DNA 60, the detection probe 104 can be employed having the unique detection sequence 106 which has been determined in advance regardless of the base sequence of the target sequence 12 in the target nucleic acid 10. The tag sequence 66 is preferably complementary such that it can specifically hybridize to the unique detection sequence 106 in the detection probe 104, and more preferably completely complementary to the detection sequence 106. The label is described hereinafter.

Primers used in the step of PCR are not specifically limited as long as the above chimeric DNA 60 can be obtained. Exemplary preferred step of PCR in the present method for detection is now described with referring to FIG. 1. The upper right of FIG. 1 shows a step of carrying out PCR on the target nucleic acid 10 and its complementary strand 20 in the sample with the first primer 30 and the second primer 40 to obtain an amplification product, chimeric DNA 60.

(First Primer)

As shown in FIG. 1, the first primer 30 contains the identification sequence 32 and the tag addition sequence 36. The first primer 30 is prepared as many as the target nucleic acids 10. When two kinds of mutations are expected at a certain part in a genomic DNA of a certain kind of an animal, which are, for example, single nucleotide substitutions with A for a wild type and T for a mutation, there are two target nucleic acids 10 for this part. Thus, one target nucleic acid 10 for this part contains the target sequence 12 having the wild type base and the other target nucleic acid 10 contains the target sequence 12 having the mutated base. Accordingly, when there are two target nucleic acids for a certain site of a gene, two first primers 30 are prepared each having the identification sequence 32 complementary to the target sequence 12 in each of the target nucleic acids 10

(Identification Sequence)

The identification sequence 32 can specifically hybridize to the target sequence 12 which is a characteristic sequence in the target nucleic acid 10, in order to identify the target nucleic acid 10. The identification sequence 32 is established to be complementary such that it can hybridize to the target sequence 12 in the target nucleic acid 10 with high selectivity, and preferably is established to be completely complementary (specific). The preferred length of the identification sequence 32 may vary according to mutations and is not specifically limited, but is preferably 15 bases or more, for example. The identification sequence 32 having 15 bases or more in length can hybridize to the target sequence 12 with high selectivity. The identification sequence 32 having 60 bases or less in length is preferable due to reduced non-specific hybridization.

(Tag Addition Sequence)

The first primer 30 may comprise the tag addition sequence 36 for adding the tag sequence 66 to the amplified product, chimeric DNA 60, so as to allow the chimeric DNA 60 being able to hybridize to the detection sequence 106 in the detection probe 104. The tag sequence 66 in the chimeric DNA 60 is for detecting the target nucleic acid 10, thus is established to be able to hybridize to the detection sequence 106 in the detection probe 104 for every target nucleic acid 10. Thus, one chimeric DNA 60 corresponding to one target nucleic acid 10 is correlated to one detection probe 104. The tag sequence 66 is preferably completely complementary to the unique detection sequence 106 in the detection probe 104. Thus, the tag addition sequence 36 preferably has the same base sequence as the unique detection sequence 106 in the detection probe 104 for detection.

As described above, the first primer 30 is prepared so as to specifically bind to the target sequence 12 in the target nucleic acid 10 and is prepared as many as the target nucleic acids 10, thereby specifically amplifying the target nucleic acids 10 while detecting the same. The first primer 30 is also formed to allow specific binding of the PCR amplified product, chimeric DNA 60, to the particular detection probe 104 which has been correlated to the target nucleic acid 10.

(Second Primer)

As shown in FIG. 1, the second primer 40 may contain the label 42 and the partial sequence 44 which is identical to the base sequence adjacent to the target sequence 12 in the target nucleic acid 10. The label 42 may be at the 5'-side of the second primer.

(Label)

The label 42 is for detecting the PCR amplified product chimeric DNA 60. The label 42 may be appropriately selected from well-known labels. The label may be any of various dyes emitting fluorescent signal after excitation such as fluorescent substances, or a substance emitting any of various signal after combining it with a secondary component by enzyme reaction or antigen-antibody reaction. The label may be typically fluorescent labeling substances such as Cy3, Alexa 555, Cy5, Alexa 647. The detection by color development may be used by combining biotin and streptoavidin-HRP and processing them with a substrate.

(Partial Sequence)

The partial sequence 44 has the same base sequence as the partial sequence 14 adjacent to the target sequence 12 in the target nucleic acid 10. The partial sequence 14 adjacent to the target sequence 12 does not mean that the partial sequence 14 is immediately at the 5'-side of the target sequence 12 without interposing one base (nucleotide) therebetween, but may be the sequence interposing appropriate number of bases (nucleotides). The partial sequence 44 in the second primer is the sequence allowing annealing of the second primer 40 to the complementary sequence 20 of the target nucleic acid 10.

When a mutation on DNA is detected, the first primer 30 and the second primer 40 are designed for the target nucleic acids 10 respectively of the wild type and the mutant. In this case, the partial sequence 44 of the second primer 40 may be common to these target nucleic acids 10. Namely, the partial sequence 44 may be a common partial sequence adjacent to the target sequence 12 in these target nucleic acids 10. The common partial sequence is a base sequence which is common regardless of the mutation. Due to this, amplification efficiency of the target nucleic acids 10 can be averaged and the amount of the first primer 40 to be used may be dec-eased. The partial sequence 44 may be the sequence having homology to multiple target nucleic acids 10 corresponding to multiple target sequences 12 constituting mutations.

As described above, the second primer 40 contains the label 42 and the partial sequence 44, and is formed so as to synthesize the chimeric DNA 60 containing the target sequence 12 due to the partial sequence 44. When the present method is to detect multiple target nucleic acids 10 having multiple target sequences 12 constituting mutations, the second primer 40 may have the common partial sequence 44 which allows amplification of multiple target nucleic acids 10 having multiple target sequences 12 constituting mutations under the same condition.

The step of obtaining the chimeric DNA 60 with the first primer 30 and the second primer 40 is now described with referring to FIGS. 1 and 3. In the following description, only PCR reaction which may give the desired chimeric DNA 60 is explained.

As shown in FIG. 3, the first primer 30 anneals to the target sequence 12 in the target nucleic acid 10 through the identification sequence 32. As a result, a new DNA strand is extended from the first primer 30 with the target nucleic acid 10 as a template, thereby synthesizing a DNA strand 50 comprising a newly synthesized partial sequence 14 (-). The obtained DNA strand 50 has the tag addition sequence 36, the identification sequence 32 and the partial sequence 14 (-).

To the partial sequence 14 (-) in the thus obtained DNA strand 50 then anneals the second primer 40 through its partial sequence 44. As a result, a new DNA strand is extended from the second primer 40 with the DNA strand 50 as a template, thereby synthesizing a DNA strand 60 comprising a base sequence complementary to the identification sequence 32 and a base sequence complementary to the tag addition sequence 36. As the identification sequence 32 has identical base sequence as a target sequence 12 (-), a base sequence complementary to the identification sequence 32 has the same sequence as the target sequence 12. As the tag addition sequence 36 is identical to the unique detection sequence 106 in the detection probe 104, a base sequence complementary to the tag addition sequence is the tag sequence 66 which is complementary to the detection sequence 106 in the detection probe 104. The thus obtained DNA strand 60 is the chimeric DNA 60 comprising the label 42 and has been correlate to the target sequence 12 and the detection probe 104. The chimeric DNA 60 is used as a template in further amplification reaction.

The step of PCR for obtaining the chimeric DNA 60 is preferably the step of asymmetric PCR. Asymmetric PCR can be carried out by varying the concentrations of the first and second primers, for example.

As the chimeric DNA 60 is obtained as a double-stranded DNA, it is dissociated to single strands for subjecting them to the step of hybridization. The dissociation in this context can be achieved by a denaturing treatment comprising chemical denaturation and thermal denaturation. When oligonucleotides linked are dissociated by chemical denaturation, a treatment known to a person skilled in the art such as alkaline denaturation may be carried out. When oligonucleotides linked are dissociated by thermal denaturation, they may be placed under a temperature of 85° C. or more, preferably 90° C. or more under physiological conditions; however, a person skilled in the art can select appropriate dissociation method.

According to the step of PCR in which the sample which may possibly contain the target nucleic acid 10 is subjected to the step of PCR, chimeric DNAs 60 can be obtained at once which can specifically detect the target nucleic acids 10 via the detection probes 104 having been correlated to the target nucleic acid 10.

A PCR reaction product may be subjected to a next step without collecting chimeric DNAs 60, because only chimeric DNAs 60 can bind to the detection probes 104 which are then detected through the label 42. Chimeric DNAs 60 may be collected by a well-known method. For example, the chimeric DNAs 50 may be separated and collected by a well-known method such as using an appropriate solid phase carrier after being dissociated into single strands.

(Step of Hybridization)

The step of hybridization is the step in which the detection probes 104 having the detection sequences 106 complementary to the tag sequences 66 in the chimeric DNAs 60 on the solid phase 100 fixed on the carrier 102 and the chimeric DNAs 60 are brought into contact so as to allow hybridization. As shown in FIGS. 1 and 2 (*c*), when the chimeric DNA 60 is complementary to the detection sequence 106 in the detection probe 104 such that they can specifically hybridize each other under certain conditions, they hybridize each other to form a double-strand at a certain detection probe 104 on the carrier 102 in this step. A washing step may further be appropriately contained following to the step of hybridization.

To the step of hybridization is provided the chimeric DNA 60 which has been synthesized in the step of PCR only when the target nucleic acid 10 is present in the sample and which hybridizes only to the detection probe 104 having been correlated. The detection sequence 106 in the detection probe 104 and the tag sequence 66 in the chimeric DNA 60 are selected with high selectivity so that mishybridization is highly suppressed, thereby highly suppressing non-specific hybridization of the chimeric DNA 60 to the detection probe 104 in the step of hybridization.

(Step of Obtaining Signal Intensity Information)

The step of obtaining signal intensity information is the step in which signal intensity information about the target nucleic acid 10 hosed in the label 42 on the carrier 102 is obtained after hybridization. According to the present step of obtaining signal intensity information, the chimeric DNA 60 hybridizes to the detection probe 104 to provide signal intensity information based on the label 42.

As shown in FIG. 1, in the step of obtaining signal intensity information, signal 48 derived from the label 42 associated with the detection probe 104 on the solid phase 100 may be detected. As the position of the detection probe 104 correlated has been already known on the solid phase 100, the presence or absence or ratio of the target nucleic acid 10 can be determined by detecting the signal 48 in the nest step of detection.

The step of obtaining signal intensity information may be carried out by selecting a conventional well-known method according to the form of the carrier 102 or the label 42. Typically, after removing non-hybridized oligonucleotides and the like from the carrier 102 by washing, fluorescent signal of the added labeling substance may be detected with an array scanner and the like or the labeling substance may be subjected to chemical luminescence reaction. When the carrier is a bead, a detection method using a flow cytometer may be employed.

(Step of Detection)

The step of detection is the step in which the presence or absence or ratio of the target nucleic acid 10 in the sample is detected based on signal intensity information of the label 42 obtained for the detection probe 104. According to the present method, even when multiple target nucleic acids 10 are detected simultaneously, the target sequences can be surely detected. According to the present method, as non-specific binding to the detection probe 104 is highly suppressed in the step of hybridization, the target nucleic acid 10 can be accurately detected with high detection sensitivity and the presence or absence or ratio thereof can be obtained.

(Primer Set)

The primer set of the present invention comprises the first and second primers described hereinabove. The primer set is used in combination with the solid phase on which the detection probes 104 have been fixed, and is suitable for obtaining the chimeric DNA described hereinabove. The first primer comprises the identification sequence 32 which is specific to the particular target nucleic acid for detecting a mutation among individuals regarding the same gene and the like or a difference between species or genera and the tag addition sequence 36 having been correlated to the detection sequence 106. The second primer comprises the label. The primer set may be for detecting two or more target nucleic acids. In this case, the primer set may comprise the first primers specific to respective target nucleic acids and the single second primer common to two or more target nucleic acids. The primer set of the present invention may be comprised in a kit together with the carrier such as the array to which the detection probes described hereinabove have been fixed.

EXAMPLE 1

The present invention is specifically described with the following examples, which do not limit the present invention.

EXAMPLE 2

The target nucleic acid was detected with the method for detection of the present invention in the present example according to the following procedures, which are now described step by step.
(1) Preparation of DNA microarray
(2) Preparation and amplification of target nucleic acids and primers
(3) Hybridization
(4) Detection with scanner
(5) Data analysis
  (1) Preparation of DNA Microarray
  On a plastic plate, aqueous solutions of synthetic oligo DNAs (Nihon Gene Research Laboratories Inc.) modified at a 3'-end with an amino group were spotted as the detection probes using a GENESHOT® spotter at NGK Insulators, Ltd. As shown in Table 1, 100 synthetic oligo DNAs were used which were D1_001 to D1_100 shown in Supplementary Table 1 in a document (Analytical Biochemistry 364 (2007) 78-85) (see FIG. 5). After spotting, the plate was baked at 80° C. for an hour. These probes are arranged in descending order of melting temperatures corresponding to Tm calculated with Visual OMP (0.1 M probe concentration, 50 mM Na+ ion and 15 mM Mg+ ion).

The synthetic oligo DNAs were fixed according to the following procedures. Namely, the plate was washed with 2×SSC/0.2% SDS for 15 minutes, with 2×SSC/0.2% SDS at 95° C. for 5 minutes, before three times of washing with sterilized water (mixing by turning vertically for 10 times). The plate was then dried by centrifugation (1000 rpm×3 minutes).

(2) Preparation of Target Nucleic Acids and Primers and Amplification

Sample genes to be detected were derived from two types of oral microorganisms, *Enterococcus faecalis* (sample 1) and *Pseudorambibacter alactolyticus* (sample 2). The length of these samples was about 150 bp, which surrounded characteristic sequences of microorganism, and artificial genes having these base sequences were used as target nucleic acids. Primers for amplifying these target nucleic acids were artificially synthesized as follows. The second primer, i.e. the forward primer (F primer) was 5'-AGGTTAAAACT-CAAAGGAATTGACG-3' (SEQ ID NO: 101), which was labeled with Cy3 at the 5'-side. The first primers, i.e. the reverse primers (R primers) were prepared according to the target sequences of the samples. The reverse primer for the sample 1 was 5'-GCAGATTCATTGGTCAGAGAA-CATATCTCTAGAGTGGT-3' (SEQ ID NO: 102) and the reverse primer for the sample 2 was 5'-CATCTAAAGCGT-TCCCAGTTCCATATCTCTATTGCGCT3' (SEQ ID) NO: 103).

These samples were amplified as follows. A reagent used for amplifying the samples was a multiple PCR kit from QIAGEN. A thermal cycler used was GeneAmp PCR System 9700 from Applied Biosystems.

The following reagents were prepared for each sample. The F primer and R primers used were respectively adjusted to 10 µmol/µl.

(Reagent Preparation)
dH$_2$O 15.0 µl
multiple PCR kit 25.0 µl
F primer 3.75 µl
R primer 3.75 µl
Sample 2.5 µl
Total 50.0 µl The prepared reagents were transferred to a thermal cycle plate and thermal cycle reaction (95° C. for 15 min; then 50 cycles of 94° C. for 30 see, 62° C. for 30 see and 72° C. for 30 min 72° C. for 10 min, and decreased to 4° C.) was carried out. The amplified labeled samples were purified with MinElute PCR Purification Kit from QIAGEN, before verifying that amplified products had a desired length.

(3) Hybridization

In order to hybridize the amplified samples obtained in (2) with the detection probes fixed on the microarray, the following Hybri control and Hybri solution were prepared, which were used for preparation of a hybridization reagent. An Alexa 555-labeled oligo DNA sequence used for Hybri control was Alexa555-rD1_100 which was obtained by labeling the 5'-end of a complementary sequence of D1_100, among those probes described in FIG. 5, with Alexa 555.

(Hybri Control)
Alexa555-rD1_100 10 µl
TE (pH 8.0) 390 µl
Total 400 µl
(Hybri Solution)
20×SSC 2.0 ml
10% SDS 0.8 ml
100% Formamide 12.0 ml
100 mM EDTA 0.8 ml
milliQ 24.4 ml
Total 40.0 ml
(Reagent for Hybridization)
Hybri control 1.5 µl
Hybri solution 9.0 µl
Subtotal 10.5 µl
Labeled sample 7.5 µl
Total 18.0 µl A prepared labeled sample solution was heated in GeneAmp PCR system 9700 from Applied Biosystems at 90° C. for 1 minute prior to heating in a heat block (TAITEC, DTU-N) at 80° C. for 1 minute. The sample solutions (9 µl each) were deposited on a spotted area of the microarray and left to stand at 37° C. for 30 minutes for hybridization reaction while preventing evaporation with Thermoblock Slide for Comfort/plus (Eppendorf).

(Washing)
After hybridization, the microarray substrate after hybridization reaction was soaked in a glass staining vat filled with washing solution having the following composition, incubated with vertical shaking for 5 minutes, and the glass substrate was transferred to a glass staining vat filled with sterilized water, incubated with vertical shaking for 1 minute, and dried by centrifugation at 2000 rpm for 1 minute to remove remaining water on the surface of the microarray substrate.
(Composition of Washing Solution)
milliQ 188.0 ml
20×SSC 10.0 ml
10% SDS 2.0 ml
Total 200.0 ml (4) Detection with Scanner Fluorescent images were obtained with ArrayWoRx from Applied Precision, Inc. by appropriately adjusting time of exposure. Fluorescent signal from the obtained images were converted to numerical values with GenePix Pro.

(5) Data Analysis

Fluorescent signal from the obtained images were converted to numerical values with GenePix Pro, which is software for numerical conversion of images. FIG. 6 shows the results of verification on whether or not the samples 1 and 2 respectively bound non-specifically to the detection probes.

As shown in FIG. 6(a), the reaction with the mixture of the samples 1 and 2 gave fluorescent signal for both probes, indicating that the samples were detected. As shown in FIGS. 6(b) and 6(c) in which either of the sample 1 or sample 2 was subjected to the reaction without mixing, it was found that non-specific binding to an undesired probe was significantly decreased. It was also found that each sample specifically bound to the respective detection probes designed to identify the respective samples.

Next, a conventional detection method of target nucleic acids (method described in Non-patent document 4) was verified as a comparative example. In the following comparative example, the target nucleic acid was detected with the conventional detection method according to the following procedures, which are now described step by step.

On a plastic plate, aqueous solutions of synthetic oligo DNAs (Nihon Gene Research Laboratories Inc.) modified at the 3'-end with an amino group were spotted as the detection probes using a GENESHOT® spotter at NGK Insulators, Ltd. The used synthetic oligo DNA sequences were 5'-AC-CACTCTAGAGATA-3' (SEQ ID NO: 104) for a sample 1, and 5'-AGCGCAATAGAGATA-3' (SEQ ID NO: 105) for a sample 2. After spotting, the plate was baked at 80° C. for an hour, and the DNAs were arranged in descending order of Tm.

Sample genes to be detected were the same samples 1 and 2 used in the example. Common primers for amplifying the target nucleic acids were artificially synthesized as follows. The F primer was 5'-AGGTTAAAACTCAAAGGAAT-TGACG-3' (SEQ ID NO: 106), which was labeled with Cy3 at the 5'-side. The R primer was 5'-ATGGTGTGACGGGCG-GTGTGT-3' (SEQ ID NO: 107).

The samples 1 and 2 were amplified by the thermal cycle reaction as described in the above (3) to (5), and hybridized with the detection probes prepared in Example 6 before washing and signal detection. FIG. 7 shows the results of verification on whether or not the samples 1 and 2 respectively bound non-specifically to the detection probes.

As shown in FIGS. 7(a) to 7(c), weak signal was detected with the detection probe for the sample 1 even when the sample did not contain the sample 1, and weak signal was detected against the detection probe for the sample 2 even when the sample did not contain the sample 2, which were thus showing non-specific binding of the samples.

The time required for hybridization in the conventional method was about two hours. Non-specific reaction to the detection probes was observed (about 10% in fluorescent intensity). On the other hand, the time required for hybridization in the present invention was decreased to about 30 minutes and non-specific reaction of the samples to undesired detection probes on the DNA microarray could be significantly reduced (less than 1% in fluorescent intensity). Thus, according to the present invention, hybridization can always be carried out at a constant temperature (about 37° C.) in about 30 minutes of tune (one-fourth of the conventional method). The present invention can also provide results with more intense signal than the conventional method, and allows more accurate detection of bases in a particular nucleic acid and more accurate determination of sequence than the conventional method. The conventional method sometimes requires optimization of hybridization conditions, re-design of probe sequences or re-preparation of arrays until desired result are obtained. On the other hand, the present invention does not require re-design of probe sequences or re-production of arrays and allows examination with arrays having the same specification all the time.

[Sequence Listing Free Text]

SEQ ID NOs: 1 to 100: probes, SEQ ID NOs: 101 to 103: primers, SEQ ID NOs: 104 and 105: probes, SEQ ID NOs: 106 and 107: primers

[Sequence Listing]

The invention claimed is:

1. A method for detection of a target nucleic acid in a sample, comprising:
    preparing a solid phase comprising detection probes respectively having different base sequences;
    carrying out PCR on the sample to obtain chimeric DNAs each having a label, and a tag sequence complementary to each of the detection probes having been correlated to the target nucleic acid;
    bringing the chimeric DNAs into contact with the detection probes such that the chimeric DNAs and the detection probes can hybridize through the tag sequences;
    obtaining signal intensity information based on the label on the solid phase; and
    detecting the target nucleic acid based on the signal intensity information;
    wherein the step of PCR comprises:
    preparing a set of primers which does not include a universal primer, wherein the set of primers consists of a first primer having an identification sequence complementary to a target sequence in the target nucleic acid and a tag addition sequence complementary to the tag sequence, and a second primer having a partial sequence that has the same sequence as a partial sequence adjacent to the target sequence and the label; and
    carrying out PCR on the sample using a set consisting of the first primer and the second primer to synthesize the chimeric DNA having the target sequence, the tag sequence and the label.

2. The method according to claim 1, wherein the step of PCR is the step of using, for two or more target nucleic acids, two or more first primers and one second primer common to the two or more target nucleic acids.

3. The method according to claim 1, wherein the step of PCR is the step of amplifying the chimeric DNAs by asymmetric PCR.

4. The method according to claim 1, wherein the target nucleic acids have a target sequence other than SNPs.

* * * * *

```
SEQUENCE LISTING

<160> NUMBER OF SEQ ID NOS: 107

<210> SEQ ID NO 1
<211> LENGTH: 23
<212> TYPE: DNA
<213> ORGANISM: Artificial
<220> FEATURE:
<223> OTHER INFORMATION: Probe

<400> SEQUENCE: 1
gcctatatga accaagccac tgc                                             23

<210> SEQ ID NO 2
<211> LENGTH: 23
<212> TYPE: DNA
<213> ORGANISM: Artificial
<220> FEATURE:
<223> OTHER INFORMATION: Probe

<400> SEQUENCE: 2
gagacaggta aaccctcaga gca                                             23

<210> SEQ ID NO 3
<211> LENGTH: 23
<212> TYPE: DNA
```

```
<213> ORGANISM: Artificial
<220> FEATURE:
<223> OTHER INFORMATION: Probe

<400> SEQUENCE: 3
gtcccaaaag cttcttacgg acg                                              23

<210> SEQ ID NO 4
<211> LENGTH: 23
<212> TYPE: DNA
<213> ORGANISM: Artificial
<220> FEATURE:
<223> OTHER INFORMATION: Probe

<400> SEQUENCE: 4
cgatcagctc tatttccctc cca                                              23

<210> SEQ ID NO 5
<211> LENGTH: 23
<212> TYPE: DNA
<213> ORGANISM: Artificial
<220> FEATURE:
<223> OTHER INFORMATION: Probe

<400> SEQUENCE: 5
gcattgaggt attgttgctc cca                                              23

<210> SEQ ID NO 6
<211> LENGTH: 23
<212> TYPE: DNA
<213> ORGANISM: Artificial
<220> FEATURE:
<223> OTHER INFORMATION: Probe

<400> SEQUENCE: 6
gcctcacttg taataagcgg gac                                              23

<210> SEQ ID NO 7
<211> LENGTH: 23
<212> TYPE: DNA
<213> ORGANISM: Artificial
<220> FEATURE:
<223> OTHER INFORMATION: Probe

<400> SEQUENCE: 7
ggggtgtgag agcttttag acg                                               23

<210> SEQ ID NO 8
<211> LENGTH: 23
<212> TYPE: DNA
<213> ORGANISM: Artificial
<220> FEATURE:
<223> OTHER INFORMATION: Probe

<400> SEQUENCE: 8
cgcgataatt gatacctacg ggc                                              23

<210> SEQ ID NO 9
<211> LENGTH: 23
<212> TYPE: DNA
<213> ORGANISM: Artificial
<220> FEATURE:
<223> OTHER INFORMATION: Probe

<400> SEQUENCE: 9
cgatcacgga ttaatgtcac ccc                                              23
```

```
<210> SEQ ID NO 10
<211> LENGTH: 23
<212> TYPE: DNA
<213> ORGANISM: Artificial
<220> FEATURE:
<223> OTHER INFORMATION: Probe

<400> SEQUENCE: 10
cgcagtttgc aagaacgaac aaa                                              23

<210> SEQ ID NO 11
<211> LENGTH: 23
<212> TYPE: DNA
<213> ORGANISM: Artificial
<220> FEATURE:
<223> OTHER INFORMATION: Probe

<400> SEQUENCE: 11
cgcgacattt agtccaggag atg                                              23

<210> SEQ ID NO 12
<211> LENGTH: 23
<212> TYPE: DNA
<213> ORGANISM: Artificial
<220> FEATURE:
<223> OTHER INFORMATION: Probe

<400> SEQUENCE: 12
accactatga ttgaggaaac gcg                                              23

<210> SEQ ID NO 13
<211> LENGTH: 23
<212> TYPE: DNA
<213> ORGANISM: Artificial
<220> FEATURE:
<223> OTHER INFORMATION: Probe

<400> SEQUENCE: 13
cgctgttggt attaccttcc tcg                                              23

<210> SEQ ID NO 14
<211> LENGTH: 23
<212> TYPE: DNA
<213> ORGANISM: Artificial
<220> FEATURE:
<223> OTHER INFORMATION: Probe

<400> SEQUENCE: 14
gagtcgaaga cctcctccta ctc                                              23

<210> SEQ ID NO 15
<211> LENGTH: 23
<212> TYPE: DNA
<213> ORGANISM: Artificial
<220> FEATURE:
<223> OTHER INFORMATION: Probe

<400> SEQUENCE: 15
tggaactggg aacgctttag atg                                              23

<210> SEQ ID NO 16
<211> LENGTH: 23
<212> TYPE: DNA
<213> ORGANISM: Artificial
<220> FEATURE:
```

-continued

<223> OTHER INFORMATION: Probe

<400> SEQUENCE: 16
cgtctttagt atcaaccctc cgc                                              23

<210> SEQ ID NO 17
<211> LENGTH: 23
<212> TYPE: DNA
<213> ORGANISM: Artificial
<220> FEATURE:
<223> OTHER INFORMATION: Probe

<400> SEQUENCE: 17 gggggggtact tcatacaaga tgc                                             23

<210> SEQ ID NO 18
<211> LENGTH: 23
<212> TYPE: DNA
<213> ORGANISM: Artificial
<220> FEATURE:
<223> OTHER INFORMATION: Probe

<400> SEQUENCE: 18
tgccgtcatt taaacgtaag ggt                                              23

<210> SEQ ID NO 19
<211> LENGTH: 23
<212> TYPE: DNA
<213> ORGANISM: Artificial
<220> FEATURE:
<223> OTHER INFORMATION: Probe

<400> SEQUENCE: 19
catctccaag aattgaccca cca                                              23

<210> SEQ ID NO 20
<211> LENGTH: 23
<212> TYPE: DNA
<213> ORGANISM: Artificial
<220> FEATURE:
<223> OTHER INFORMATION: Probe

<400> SEQUENCE: 20
atgccgttgt caagagttat ggt                                              23

<210> SEQ ID NO 21
<211> LENGTH: 23
<212> TYPE: DNA
<213> ORGANISM: Artificial
<220> FEATURE:
<223> OTHER INFORMATION: Probe

<400> SEQUENCE: 21
cgagagtctg taatagccga tgc                                              23

<210> SEQ ID NO 22
<211> LENGTH: 23
<212> TYPE: DNA
<213> ORGANISM: Artificial
<220> FEATURE:
<223> OTHER INFORMATION: Probe

<400> SEQUENCE: 22
cacgcttagt tcctaccttta ggc                                             23

```
<210> SEQ ID NO 23
<211> LENGTH: 23
<212> TYPE: DNA
<213> ORGANISM: Artificial
<220> FEATURE:
<223> OTHER INFORMATION: Probe

<400> SEQUENCE: 23
gcccgggaat agattataac gca                                              23

<210> SEQ ID NO 24
<211> LENGTH: 23
<212> TYPE: DNA
<213> ORGANISM: Artificial
<220> FEATURE:
<223> OTHER INFORMATION: Probe

<400> SEQUENCE: 24 gcagcccttα tagataacgg gac                                              23

<210> SEQ ID NO 25
<211> LENGTH: 23
<212> TYPE: DNA
<213> ORGANISM: Artificial
<220> FEATURE:
<223> OTHER INFORMATION: Probe

<400> SEQUENCE: 25
cgctctggtt actattggac gtt                                              23

<210> SEQ ID NO 26
<211> LENGTH: 23
<212> TYPE: DNA
<213> ORGANISM: Artificial
<220> FEATURE:
<223> OTHER INFORMATION: Probe

<400> SEQUENCE: 26
gcatttttag taatccgagc gcc                                              23

<210> SEQ ID NO 27
<211> LENGTH: 23
<212> TYPE: DNA
<213> ORGANISM: Artificial
<220> FEATURE:
<223> OTHER INFORMATION: Probe

<400> SEQUENCE: 27
cgccattata caacggttca tgc                                              23

<210> SEQ ID NO 28
<211> LENGTH: 23
<212> TYPE: DNA
<213> ORGANISM: Artificial
<220> FEATURE:
<223> OTHER INFORMATION: Probe

<400> SEQUENCE: 28
ggctggttaa atgtaaatcc gcg                                              23

<210> SEQ ID NO 29
<211> LENGTH: 23
<212> TYPE: DNA
<213> ORGANISM: Artificial
<220> FEATURE:
<223> OTHER INFORMATION: Probe
```

```
<400> SEQUENCE: 29
gtcggtatcg aaaaggtact gca                                          23

<210> SEQ ID NO 30
<211> LENGTH: 23
<212> TYPE: DNA
<213> ORGANISM: Artificial
<220> FEATURE:
<223> OTHER INFORMATION: Probe

<400> SEQUENCE: 30
cgccaatgac aataagttga ggc                                          23

<210> SEQ ID NO 31
<211> LENGTH: 23
<212> TYPE: DNA
<213> ORGANISM: Artificial
<220> FEATURE:
<223> OTHER INFORMATION: Probe

<400> SEQUENCE: 31
ggtcgtaaca ttgagaggag acg                                          23

<210> SEQ ID NO 32
<211> LENGTH: 23
<212> TYPE: DNA
<213> ORGANISM: Artificial
<220> FEATURE:
<223> OTHER INFORMATION: Probe

<400> SEQUENCE: 32
gaagccatga tactgttcag ggt                                          23

<210> SEQ ID NO 33
<211> LENGTH: 23
<212> TYPE: DNA
<213> ORGANISM: Artificial
<220> FEATURE:
<223> OTHER INFORMATION: Probe

<400> SEQUENCE: 33
aggcagttca acctatatct gcg                                          23

<210> SEQ ID NO 34
<211> LENGTH: 23
<212> TYPE: DNA
<213> ORGANISM: Artificial
<220> FEATURE:
<223> OTHER INFORMATION: Probe

<400> SEQUENCE: 34
gcctcacata actggagaaa cct                                          23

<210> SEQ ID NO 35
<211> LENGTH: 23
<212> TYPE: DNA
<213> ORGANISM: Artificial
<220> FEATURE:
<223> OTHER INFORMATION: Probe

<400> SEQUENCE: 35
gcatatagtg acggtaaggc gaa                                          23

<210> SEQ ID NO 36
<211> LENGTH: 23
```

```
<212> TYPE: DNA
<213> ORGANISM: Artificial
<220> FEATURE:
<223> OTHER INFORMATION: Probe

<400> SEQUENCE: 36
tgccggttat acctttaagg acg                                            23

<210> SEQ ID NO 37
<211> LENGTH: 23
<212> TYPE: DNA
<213> ORGANISM: Artificial
<220> FEATURE:
<223> OTHER INFORMATION: Probe

<400> SEQUENCE: 37
gcctatagtg tcgattgtcc tcg                                            23

<210> SEQ ID NO 38
<211> LENGTH: 23
<212> TYPE: DNA
<213> ORGANISM: Artificial
<220> FEATURE:
<223> OTHER INFORMATION: Probe

<400> SEQUENCE: 38
ggctcgtagt actccttaca tgc                                            23

<210> SEQ ID NO 39
<211> LENGTH: 23
<212> TYPE: DNA
<213> ORGANISM: Artificial
<220> FEATURE:
<223> OTHER INFORMATION: Probe

<400> SEQUENCE: 39
ctagtccatt gtaacgaagg cca                                            23

<210> SEQ ID NO 40
<211> LENGTH: 23
<212> TYPE: DNA
<213> ORGANISM: Artificial
<220> FEATURE:
<223> OTHER INFORMATION: Probe

<400> SEQUENCE: 40
ccgtcgtgtt attaaagacc cct                                            23

<210> SEQ ID NO 41
<211> LENGTH: 23
<212> TYPE: DNA
<213> ORGANISM: Artificial
<220> FEATURE:
<223> OTHER INFORMATION: Probe

<400> SEQUENCE: 41
ccgtgtgtat gagtatgaca gca                                            23

<210> SEQ ID NO 42
<211> LENGTH: 23
<212> TYPE: DNA
<213> ORGANISM: Artificial
<220> FEATURE:
<223> OTHER INFORMATION: Probe

<400> SEQUENCE: 42
```

```
tgccggctat cgtaagtata tgc                                              23

<210> SEQ ID NO 43
<211> LENGTH: 23
<212> TYPE: DNA
<213> ORGANISM: Artificial
<220> FEATURE:
<223> OTHER INFORMATION: Probe

<400> SEQUENCE: 43
gggataggta ttatgctcca gcc                                              23

<210> SEQ ID NO 44
<211> LENGTH: 23
<212> TYPE: DNA
<213> ORGANISM: Artificial
<220> FEATURE:
<223> OTHER INFORMATION: Probe

<400> SEQUENCE: 44
ccatcagtta ttcggaggga ctc                                              23

<210> SEQ ID NO 45
<211> LENGTH: 23
<212> TYPE: DNA
<213> ORGANISM: Artificial
<220> FEATURE:
<223> OTHER INFORMATION: Probe

<400> SEQUENCE: 45
agtcgcttaa ttactccgga tgg                                              23

<210> SEQ ID NO 46
<211> LENGTH: 23
<212> TYPE: DNA
<213> ORGANISM: Artificial
<220> FEATURE:
<223> OTHER INFORMATION: Probe

<400> SEQUENCE: 46
gcagctgaat tgctatgatc acc                                              23

<210> SEQ ID NO 47
<211> LENGTH: 23
<212> TYPE: DNA
<213> ORGANISM: Artificial
<220> FEATURE:
<223> OTHER INFORMATION: Probe

<400> SEQUENCE: 47
gcacctcata ccttcataga gca                                              23

<210> SEQ ID NO 48
<211> LENGTH: 23
<212> TYPE: DNA
<213> ORGANISM: Artificial
<220> FEATURE:
<223> OTHER INFORMATION: Probe

<400> SEQUENCE: 48
agtcagtcca aatctcagga tgg                                              23

<210> SEQ ID NO 49
<211> LENGTH: 23
<212> TYPE: DNA
<213> ORGANISM: Artificial
```

<220> FEATURE:
<223> OTHER INFORMATION: Probe

<400> SEQUENCE: 49
aggtccggta gtaatttagg tgc       23

<210> SEQ ID NO 50
<211> LENGTH: 23
<212> TYPE: DNA
<213> ORGANISM: Artificial
<220> FEATURE:
<223> OTHER INFORMATION: Probe

<400> SEQUENCE: 50
cgcctaaatg aaactcactc tgc       23

<210> SEQ ID NO 51
<211> LENGTH: 23
<212> TYPE: DNA
<213> ORGANISM: Artificial
<220> FEATURE:
<223> OTHER INFORMATION: Probe

<400> SEQUENCE: 51
gcccacactc ttacttatcg act       23

<210> SEQ ID NO 52
<211> LENGTH: 23
<212> TYPE: DNA
<213> ORGANISM: Artificial
<220> FEATURE:
<223> OTHER INFORMATION: Probe

<400> SEQUENCE: 52
ttcgcttcgt tgtaatttcg gac       23

<210> SEQ ID NO 53
<211> LENGTH: 23
<212> TYPE: DNA
<213> ORGANISM: Artificial
<220> FEATURE:
<223> OTHER INFORMATION: Probe

<400> SEQUENCE: 53
agacaattag aatcagtgcc cct       23

<210> SEQ ID NO 54
<211> LENGTH: 23
<212> TYPE: DNA
<213> ORGANISM: Artificial
<220> FEATURE:
<223> OTHER INFORMATION: Probe

<400> SEQUENCE: 54
agtcagttaa tcagacgtga gca       23

<210> SEQ ID NO 55
<211> LENGTH: 23
<212> TYPE: DNA
<213> ORGANISM: Artificial
<220> FEATURE:
<223> OTHER INFORMATION: Probe

<400> SEQUENCE: 55
cgcggtacta ttagaaaggg cta       23

```
<210> SEQ ID NO 56
<211> LENGTH: 23
<212> TYPE: DNA
<213> ORGANISM: Artificial
<220> FEATURE:
<223> OTHER INFORMATION: Probe

<400> SEQUENCE: 56
ggctctacaa acttgtgtcc atg                                              23

<210> SEQ ID NO 57
<211> LENGTH: 23
<212> TYPE: DNA
<213> ORGANISM: Artificial
<220> FEATURE:
<223> OTHER INFORMATION: Probe

<400> SEQUENCE: 57
cgatcatgta aagctaactc gcg                                              23

<210> SEQ ID NO 58
<211> LENGTH: 23
<212> TYPE: DNA
<213> ORGANISM: Artificial
<220> FEATURE:
<223> OTHER INFORMATION: Probe

<400> SEQUENCE: 58
tagcacccgt taaaacggaa atg                                              23

<210> SEQ ID NO 59
<211> LENGTH: 23
<212> TYPE: DNA
<213> ORGANISM: Artificial
<220> FEATURE:
<223> OTHER INFORMATION: Probe

<400> SEQUENCE: 59
tttgttgttc gatatcaggc gtg                                              23

<210> SEQ ID NO 60
<211> LENGTH: 23
<212> TYPE: DNA
<213> ORGANISM: Artificial
<220> FEATURE:
<223> OTHER INFORMATION: Probe

<400> SEQUENCE: 60
gcactaccgc taactatacg cta                                              23

<210> SEQ ID NO 61
<211> LENGTH: 23
<212> TYPE: DNA
<213> ORGANISM: Artificial
<220> FEATURE:
<223> OTHER INFORMATION: Probe

<400> SEQUENCE: 61
tatgtttagt tgttgaaccg gcg                                              23

<210> SEQ ID NO 62
<211> LENGTH: 23
<212> TYPE: DNA
<213> ORGANISM: Artificial
<220> FEATURE:
<223> OTHER INFORMATION: Probe
```

-continued

```
<400> SEQUENCE: 62
tggcaattac agttgttaac gca                                             23

<210> SEQ ID NO 63
<211> LENGTH: 23
<212> TYPE: DNA
<213> ORGANISM: Artificial
<220> FEATURE:
<223> OTHER INFORMATION: Probe

<400> SEQUENCE: 63
cgcgatataa cattaaccga ggc                                             23

<210> SEQ ID NO 64
<211> LENGTH: 23
<212> TYPE: DNA
<213> ORGANISM: Artificial
<220> FEATURE:
<223> OTHER INFORMATION: Probe

<400> SEQUENCE: 64
ggggtcaaac caacaattga tct                                             23

<210> SEQ ID NO 65
<211> LENGTH: 23
<212> TYPE: DNA
<213> ORGANISM: Artificial
<220> FEATURE:
<223> OTHER INFORMATION: Probe

<400> SEQUENCE: 65
tggcaataca ataacgtatc gcg                                             23

<210> SEQ ID NO 66
<211> LENGTH: 23
<212> TYPE: DNA
<213> ORGANISM: Artificial
<220> FEATURE:
<223> OTHER INFORMATION: Probe

<400> SEQUENCE: 66
aggcatccta agaaatcgct act                                             23

<210> SEQ ID NO 67
<211> LENGTH: 23
<212> TYPE: DNA
<213> ORGANISM: Artificial
<220> FEATURE:
<223> OTHER INFORMATION: Probe

<400> SEQUENCE: 67
gagtagcagg caaataccct aga                                             23

<210> SEQ ID NO 68
<211> LENGTH: 23
<212> TYPE: DNA
<213> ORGANISM: Artificial
<220> FEATURE:
<223> OTHER INFORMATION: Probe

<400> SEQUENCE: 68
cgcgattcct attgattgat ccc                                             23

<210> SEQ ID NO 69
```

```
<210> SEQ ID NO 69
<211> LENGTH: 23
<212> TYPE: DNA
<213> ORGANISM: Artificial
<220> FEATURE:
<223> OTHER INFORMATION: Probe

<400> SEQUENCE: 69
gcccattgat agaattacga ggc                                              23

<210> SEQ ID NO 70
<211> LENGTH: 23
<212> TYPE: DNA
<213> ORGANISM: Artificial
<220> FEATURE:
<223> OTHER INFORMATION: Probe

<400> SEQUENCE: 70
gagtccgcaa aaatatagga ggc                                              23

<210> SEQ ID NO 71
<211> LENGTH: 23
<212> TYPE: DNA
<213> ORGANISM: Artificial
<220> FEATURE:
<223> OTHER INFORMATION: Probe

<400> SEQUENCE: 71
tgccgtgata cttaactacg cta                                              23

<210> SEQ ID NO 72
<211> LENGTH: 23
<212> TYPE: DNA
<213> ORGANISM: Artificial
<220> FEATURE:
<223> OTHER INFORMATION: Probe

<400> SEQUENCE: 72
ttcggttgtc gatatgagga tct                                              23

<210> SEQ ID NO 73
<211> LENGTH: 23
<212> TYPE: DNA
<213> ORGANISM: Artificial
<220> FEATURE:
<223> OTHER INFORMATION: Probe

<400> SEQUENCE: 73
cgcgtcgaat tacttaatca cca                                              23

<210> SEQ ID NO 74
<211> LENGTH: 23
<212> TYPE: DNA
<213> ORGANISM: Artificial
<220> FEATURE:
<223> OTHER INFORMATION: Probe

<400> SEQUENCE: 74
gaaggatcgc ttttatctgg cat                                              23

<210> SEQ ID NO 75
<211> LENGTH: 23
<212> TYPE: DNA
<213> ORGANISM: Artificial
<220> FEATURE:
<223> OTHER INFORMATION: Probe

<400> SEQUENCE: 75
```
ggcgatttat tgctaactgg cta    23

<210> SEQ ID NO 76
<211> LENGTH: 23
<212> TYPE: DNA
<213> ORGANISM: Artificial
<220> FEATURE:
<223> OTHER INFORMATION: Probe

<400> SEQUENCE: 76
ggtggagtga atctcactag act    23

<210> SEQ ID NO 77
<211> LENGTH: 23
<212> TYPE: DNA
<213> ORGANISM: Artificial
<220> FEATURE:
<223> OTHER INFORMATION: Probe

<400> SEQUENCE: 77
gcatacgaac ttctatatcg gcg    23

<210> SEQ ID NO 78
<211> LENGTH: 23
<212> TYPE: DNA
<213> ORGANISM: Artificial
<220> FEATURE:
<223> OTHER INFORMATION: Probe

<400> SEQUENCE: 78
tgcactctga tatatacagg cca    23

<210> SEQ ID NO 79
<211> LENGTH: 23
<212> TYPE: DNA
<213> ORGANISM: Artificial
<220> FEATURE:
<223> OTHER INFORMATION: Probe

<400> SEQUENCE: 79
ccgtctgggt taaagattgc tag    23

<210> SEQ ID NO 80
<211> LENGTH: 23
<212> TYPE: DNA
<213> ORGANISM: Artificial
<220> FEATURE:
<223> OTHER INFORMATION: Probe

<400> SEQUENCE: 80
aagagattta acttgagctc gcc    23

<210> SEQ ID NO 81
<211> LENGTH: 23
<212> TYPE: DNA
<213> ORGANISM: Artificial
<220> FEATURE:
<223> OTHER INFORMATION: Probe

<400> SEQUENCE: 81
tgttctctga ccaatgaatc tgc    23

<210> SEQ ID NO 82
<211> LENGTH: 23
<212> TYPE: DNA

```
<213> ORGANISM: Artificial
<220> FEATURE:
<223> OTHER INFORMATION: Probe

<400> SEQUENCE: 82
gggatccgta acaagtgtgt tag                                              23

<210> SEQ ID NO 83
<211> LENGTH: 23
<212> TYPE: DNA
<213> ORGANISM: Artificial
<220> FEATURE:
<223> OTHER INFORMATION: Probe

<400> SEQUENCE: 83
tagcccagtg atttatgaca tgc                                              23

<210> SEQ ID NO 84
<211> LENGTH: 23
<212> TYPE: DNA
<213> ORGANISM: Artificial
<220> FEATURE:
<223> OTHER INFORMATION: Probe

<400> SEQUENCE: 84
ccatatccga ttattagcga cgg                                              23

<210> SEQ ID NO 85
<211> LENGTH: 23
<212> TYPE: DNA
<213> ORGANISM: Artificial
<220> FEATURE:
<223> OTHER INFORMATION: Probe

<400> SEQUENCE: 85
tgctcactta cattacgtcc atg                                              23

<210> SEQ ID NO 86
<211> LENGTH: 23
<212> TYPE: DNA
<213> ORGANISM: Artificial
<220> FEATURE:
<223> OTHER INFORMATION: Probe

<400> SEQUENCE: 86
catttgtcag gtacagtcca ctt                                              23

<210> SEQ ID NO 87
<211> LENGTH: 23
<212> TYPE: DNA
<213> ORGANISM: Artificial
<220> FEATURE:
<223> OTHER INFORMATION: Probe

<400> SEQUENCE: 87
catggataag ttttcaagct gcg                                              23

<210> SEQ ID NO 88
<211> LENGTH: 23
<212> TYPE: DNA
<213> ORGANISM: Artificial
<220> FEATURE:
<223> OTHER INFORMATION: Probe

<400> SEQUENCE: 88
cgctgttact gtaagcgtac tag                                              23
```

<210> SEQ ID NO 89
<211> LENGTH: 23
<212> TYPE: DNA
<213> ORGANISM: Artificial
<220> FEATURE:
<223> OTHER INFORMATION: Probe

<400> SEQUENCE: 89
tgctgtcttc gtgttttacc tag                                              23

<210> SEQ ID NO 90
<211> LENGTH: 23
<212> TYPE: DNA
<213> ORGANISM: Artificial
<220> FEATURE:
<223> OTHER INFORMATION: Probe

<400> SEQUENCE: 90
tacacctatc aactcgtaga gca                                              23

<210> SEQ ID NO 91
<211> LENGTH: 23
<212> TYPE: DNA
<213> ORGANISM: Artificial
<220> FEATURE:
<223> OTHER INFORMATION: Probe

<400> SEQUENCE: 91
cgccgtcagt acttgtatag atg                                              23

<210> SEQ ID NO 92
<211> LENGTH: 23
<212> TYPE: DNA
<213> ORGANISM: Artificial
<220> FEATURE:
<223> OTHER INFORMATION: Probe

<400> SEQUENCE: 92
tattctacca acgacatcac tgc                                              23

<210> SEQ ID NO 93
<211> LENGTH: 23
<212> TYPE: DNA
<213> ORGANISM: Artificial
<220> FEATURE:
<223> OTHER INFORMATION: Probe

<400> SEQUENCE: 93
cattcgacat aagctgttga tgc                                              23

<210> SEQ ID NO 94
<211> LENGTH: 23
<212> TYPE: DNA
<213> ORGANISM: Artificial
<220> FEATURE:
<223> OTHER INFORMATION: Probe

<400> SEQUENCE: 94
tgcagtgtaa gcaactattg tct                                              23

<210> SEQ ID NO 95
<211> LENGTH: 23
<212> TYPE: DNA
<213> ORGANISM: Artificial
<220> FEATURE:

-continued

<223> OTHER INFORMATION: Probe

<400> SEQUENCE: 95
ctaggtacaa caccaactgt ctc                                    23

<210> SEQ ID NO 96
<211> LENGTH: 23
<212> TYPE: DNA
<213> ORGANISM: Artificial
<220> FEATURE:
<223> OTHER INFORMATION: Probe

<400> SEQUENCE: 96
gcctattaag gtctacgtca tcg                                    23

<210> SEQ ID NO 97
<211> LENGTH: 23
<212> TYPE: DNA
<213> ORGANISM: Artificial
<220> FEATURE:
<223> OTHER INFORMATION: Probe

<400> SEQUENCE: 97
atgccaatat gtactcgtga ctc                                    23

<210> SEQ ID NO 98
<211> LENGTH: 23
<212> TYPE: DNA
<213> ORGANISM: Artificial
<220> FEATURE:
<223> OTHER INFORMATION: Probe

<400> SEQUENCE: 98
agtcatacag tgaggaccaa atg                                    23

<210> SEQ ID NO 99
<211> LENGTH: 23
<212> TYPE: DNA
<213> ORGANISM: Artificial
<220> FEATURE:
<223> OTHER INFORMATION: Probe

<400> SEQUENCE: 99
tagccaactc taaataacgg acg                                    23

<210> SEQ ID NO 100
<211> LENGTH: 23
<212> TYPE: DNA
<213> ORGANISM: Artificial
<220> FEATURE:
<223> OTHER INFORMATION: Probe

<400> SEQUENCE: 100
ctagcacaat taatcaatcc gcc                                    23

<210> SEQ ID NO 101
<211> LENGTH: 25
<212> TYPE: DNA
<213> ORGANISM: Artificial Sequence
<220> FEATURE:
<223> OTHER INFORMATION: Primer

<400> SEQUENCE: 101
aggttaaaac tcaaaggaat tgacg                                  25

```
<210> SEQ ID NO 102
<211> LENGTH: 38
<212> TYPE: DNA
<213> ORGANISM: Artificial Sequence
<220> FEATURE:
<223> OTHER INFORMATION: Primer

<400> SEQUENCE: 102
gcagattcat tggtcagaga acatatctct agagtggt                             38

<210> SEQ ID NO 103
<211> LENGTH: 38
<212> TYPE: DNA
<213> ORGANISM: Artificial Sequence
<220> FEATURE:
<223> OTHER INFORMATION: Primer

<400> SEQUENCE: 103
catctaaagc gttcccagtt ccatatctct attgcgct                             38

<210> SEQ ID NO 104
<211> LENGTH: 15
<212> TYPE: DNA
<213> ORGANISM: Artificial Sequence
<220> FEATURE:
<223> OTHER INFORMATION: Probe

<400> SEQUENCE: 104
accactctag agata                                                      15

<210> SEQ ID NO 105
<211> LENGTH: 15
<212> TYPE: DNA
<213> ORGANISM: Artificial Sequence
<220> FEATURE:
<223> OTHER INFORMATION: Probe

<400> SEQUENCE: 105
agcgcaatag agata                                                      15

<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
aggttaaaac tcaaaggaat tgacg                                           25

<210> SEQ ID NO 107
<211> LENGTH: 21
<212> TYPE: DNA
<213> ORGANISM: Artificial Sequence
<220> FEATURE:
<223> OTHER INFORMATION: Primer

<400> SEQUENCE: 107
atggtgtgac gggcggtgtg t                                               21
```